US012558045B2

(12) United States Patent
Chern

(10) Patent No.: US 12,558,045 B2
(45) Date of Patent: Feb. 24, 2026

(54) SUB-SYSTEM X-RAY SOURCE MODULE

(71) Applicant: X-Sight Incorporated, Cambridge, MA (US)

(72) Inventor: Winston Chern, Cambridge, MA (US)

(73) Assignee: X-SIGHT INCORPORATED, Cambridge, MA (US)

( * ) Notice: Subject to any disclaimer, the term of this patent is extended or adjusted under 35 U.S.C. 154(b) by 266 days.

(21) Appl. No.: 18/093,425

(22) Filed: Jan. 5, 2023

(65) Prior Publication Data

US 2023/0210484 A1     Jul. 6, 2023

Related U.S. Application Data

(60) Provisional application No. 63/341,580, filed on May 13, 2022, provisional application No. 63/296,551, filed on Jan. 5, 2022.

(51) Int. Cl.
*A61B 6/00* (2024.01)
*A61B 6/03* (2006.01)

(52) U.S. Cl.
CPC ............ *A61B 6/4441* (2013.01); *A61B 6/035* (2013.01); *A61B 6/4405* (2013.01); *A61B 6/547* (2013.01); *A61B 6/56* (2013.01)

(58) Field of Classification Search
CPC ..... A61B 6/4441; A61B 6/035; A61B 6/4405; A61B 6/547; A61B 6/0407; A61B 6/06; A61B 6/4007; A61B 6/4035; A61B 6/4233; A61B 6/4266; A61B 6/54; A61B 6/032; A61B 6/4291
See application file for complete search history.

(56) References Cited

U.S. PATENT DOCUMENTS

| | | |
|---|---|---|
| 2002/0150215 A1 | 10/2002 | Barnes et al. |
| 2004/0170254 A1 | 9/2004 | Gregerson et al. |
| 2005/0135560 A1* | 6/2005 | Dafni ........................ A61B 6/56 |
| | | 378/101 |
| 2009/0161816 A1* | 6/2009 | De Man ............... A61B 6/4028 |
| | | 378/92 |
| 2011/0002439 A1 | 1/2011 | Zhang |
| 2012/0256099 A1 | 10/2012 | Gregerson et al. |
| 2014/0046212 A1 | 2/2014 | Deutschmann |
| 2015/0131775 A1* | 5/2015 | Yorkston .............. A61B 6/4405 |
| | | 378/17 |
| 2019/0083050 A1 | 3/2019 | Wang et al. |
| 2020/0406064 A1 | 12/2020 | Maltz et al. |
| 2023/0375484 A1* | 11/2023 | Inscoe ..................... A61B 6/51 |

OTHER PUBLICATIONS

International Preliminary Report on Patentability issued by the International Bureau of WIPO in connection with International Application No. PCT/US2023/010170, dated Jun. 20, 2024.
International Search Report and Written Opinion issued by the ISA/US, Commissioner for Patents in connection with International Application No. PCT/US2023/10170, dated Apr. 21, 2023.

* cited by examiner

*Primary Examiner* — David J Makiya
*Assistant Examiner* — Mamadou Faye
(74) *Attorney, Agent, or Firm* — Carter, DeLuca & Farrell LLP; George Likourezos

(57) ABSTRACT

A modular x-ray imaging system includes an application specific module, a base unit in communication with the application specific module, and a mechanical support configured to support the x-ray application specific module. The base unit and application specific module are configured to communicate by wired and/or wireless communication.

15 Claims, 11 Drawing Sheets

SUB-SYSTEM X-RAY SOURCE MODULE

CROSS-REFERENCE TO RELATED APPLICATION/CLAIM OF PRIORITY

This application claims the benefit of, and priority to, U.S. Provisional Patent Application 63/341,580, filed on May 13, 2022, and U.S. Provisional Patent Application No. 63/296,551, filed on Jan. 5, 2022, the entire contents of which are hereby incorporated herein by reference.

TECHNICAL FIELD

The present disclosure relates to a system design for x-ray imaging equipment including digital radiography, fluoroscopy, tomosynthesis, and computed tomography (CT).

BACKGROUND

X-ray imaging is a key technology for medical diagnostics, surgical guidance, and industrial imaging, which provides operators the ability to non-destructively image the content of objects. Systems are currently fully integrated with all of their components incorporated into their respective systems which include the computer, data acquisition system (DAS), x-ray source, x-ray detectors, high voltage power supply, and cooling. For systems with 3D imaging such as tomosynthesis and computed tomography, the systems also contain a means to move the x-ray source and detectors such as a motor, a gantry of significant stiffness to provide accurate motion, and/or a method of maintaining the connection to the x-ray source and collecting data from the x-ray detectors while under motion such as a slip ring. The integrated system is fundamentally limited in portability due its large size and weight and has high costs for each individual system component (>$100,000 per system and sometimes >$1,000,000 per system).

SUMMARY

An aspect of the present disclosure provides a modular x-ray imaging system that includes an application specific module, a base unit, and a mechanical support. The application specific module includes an imaging ring configured to image a patient; a sensor configured to provide positioning data to enable positioning of the imaging ring relative to the patient; a motor configured to position the imaging ring based on the sensed position; and a controller for controlling an output of the plurality of x-ray sources. The imaging ring includes a plurality of x-ray sources configured to generate and emit a beam including an x-ray spectrum; one or more collimators configured to restrict the span of an x-ray beam; one or more filters configured to selectively attenuate and/or block low-energy rays during x-ray imaging; and one or more x-ray detectors configured to detect x-rays generated by the plurality of x-ray sources. The base unit is in communication with the application specific module. The base unit includes a first power supply having an output voltage greater than 10 kV; a second power supply having an output voltage less than 10 kV configured to turn on and off each individual x-ray source of the plurality of x-ray sources; a processor; and a memory. The memory includes instructions stored thereon which, when executed by the processor, cause the modular x-ray imaging system to position the imaging ring based on the sensor and capture imaging data. The mechanical support is configured to support the imaging ring.

In an aspect of the present disclosure, the base unit may further include a battery. The base unit may be configured to operate solely on battery power with part of the battery being able to be changed during operation to maintain battery power longer than a total capacity of the battery.

In an aspect of the present disclosure, the base unit may be configured to move independently of the rest of the x-ray imaging system.

In another aspect of the present disclosure, the base unit may be configured to be connected to, control, and power multiple application specific modules simultaneously.

In an aspect of the present disclosure, the system may further include a second application specific module configured to provide convertible computed tomography (CT) which can operate vertically, or laterally, and any angle in-between.

In an aspect of the present disclosure, the application specific module may be operated as at least one of a vertical or a horizontal CT.

In an aspect of the present disclosure, when operating laterally, the system may further include an x-ray transparent table configured to support a patient with the x-ray transparent table supported by at least two points each on a different half of the table with an opening for the region of interest for imaging.

In an aspect of the present disclosure, the second application specific module may further include: motorized controls; an imaging ring including a controller, a plurality of x-ray sources, one or more anti-scatter grids, x-ray detectors, and communication electronics; a motorized track configured to move motorized controls and an imaging ring; and a sensor configured to position the imaging ring relative to the patient. The motorized controls may provide mechanical alignment of the ring to the patient;

In another aspect of the present disclosure, the motorized track may be configured to move the second application specific module a distance larger than the desired imaging field of view and less than the length of the full body.

In an aspect of the present disclosure, the motorized track may be configured to be rotated around an axis normal to a surface of contact with the mechanical support in order to change a direction of motion.

In an aspect of the present disclosure, the motorized controls may be further configured to move the imaging ring in the x-y plane of the patient using at least one linear degree of motion and at least one angular degree of freedom.

In another aspect of the present disclosure, the system further may include a dynamic anti-scatter grid or a moving anti-scatter grid with a plurality of x-ray sources to optimally remove scatter from each x-ray source.

In an aspect of the present disclosure, the application specific module may be configured to be adjusted in height and/or rotation relative to the normal of a mounting surface of the application specific module.

In an aspect of the present disclosure, the system may further include at least one wired or wireless connection between the application specific module and the base unit with at least one high voltage connection of greater than 10 kV configured to connect the high voltage power supply to the application specific module; and at least one or more low voltage connections of less than 10 kV configured to connect between the power supply configured for powering the motors, a low voltage power supply, and the processor to the application specific module to provide control of the x-ray sources and communication between the data acquisition system and the sensors controlling the positioning of the application specific module.

An aspect of the present disclosure provides an x-ray source alignment apparatus that includes an imaging ring including a plurality of individually packaged x-ray sources configured to emit a beam including an x-ray spectrum; a second sensor configured to provide positioning data to enable positioning of the imaging ring to the patient; a motorized control configured to provide mechanical alignment of the imaging ring to a patient based on the positioning data; and a motorized track configured to move the motorized controls and the imaging ring based on the positioning data.

In an aspect of the present disclosure, the plurality of individually packaged x-ray sources may include at least one focal spot configured for imaging.

In an aspect of the present disclosure, the plurality of individually packaged x-ray sources may further include a filter configured to reduce an intensity of one or more wavelengths from the x-ray spectrum.

In an aspect of the present disclosure, the plurality of individually packaged x-ray sources may further include a collimator configured to direct the x-ray beam.

In an aspect of the present disclosure, the x-ray source alignment apparatus may include a sensor configured to determine the position of the imaging ring relative to the patient.

In another aspect of the present disclosure, a modular x-ray imaging system includes an application specific module; a base unit in communication with the application specific module and configured to power the application specific module; and a mechanical support. The application specific module includes a vertically positionable imaging ring configured to image a patient; a processor; and a memory. The base unit and application specific module are configured to communicate in at least one of a wired and/or wireless manner. The memory includes instructions stored thereon which, when executed by the processor, cause the modular x-ray imaging system to position the imaging ring and capture imaging data. The mechanical support is configured to support the vertically positionable imaging ring.

Further details and aspects of the present disclosure are described in more detail below with reference to the appended drawings.

BRIEF DESCRIPTION OF THE DRAWINGS

A better understanding of the features and advantages of the present disclosure will be obtained by reference to the following detailed description that sets forth illustrative aspects in which the principles of the present disclosure are utilized, and the accompanying drawings, of which.

4

Figure 7:
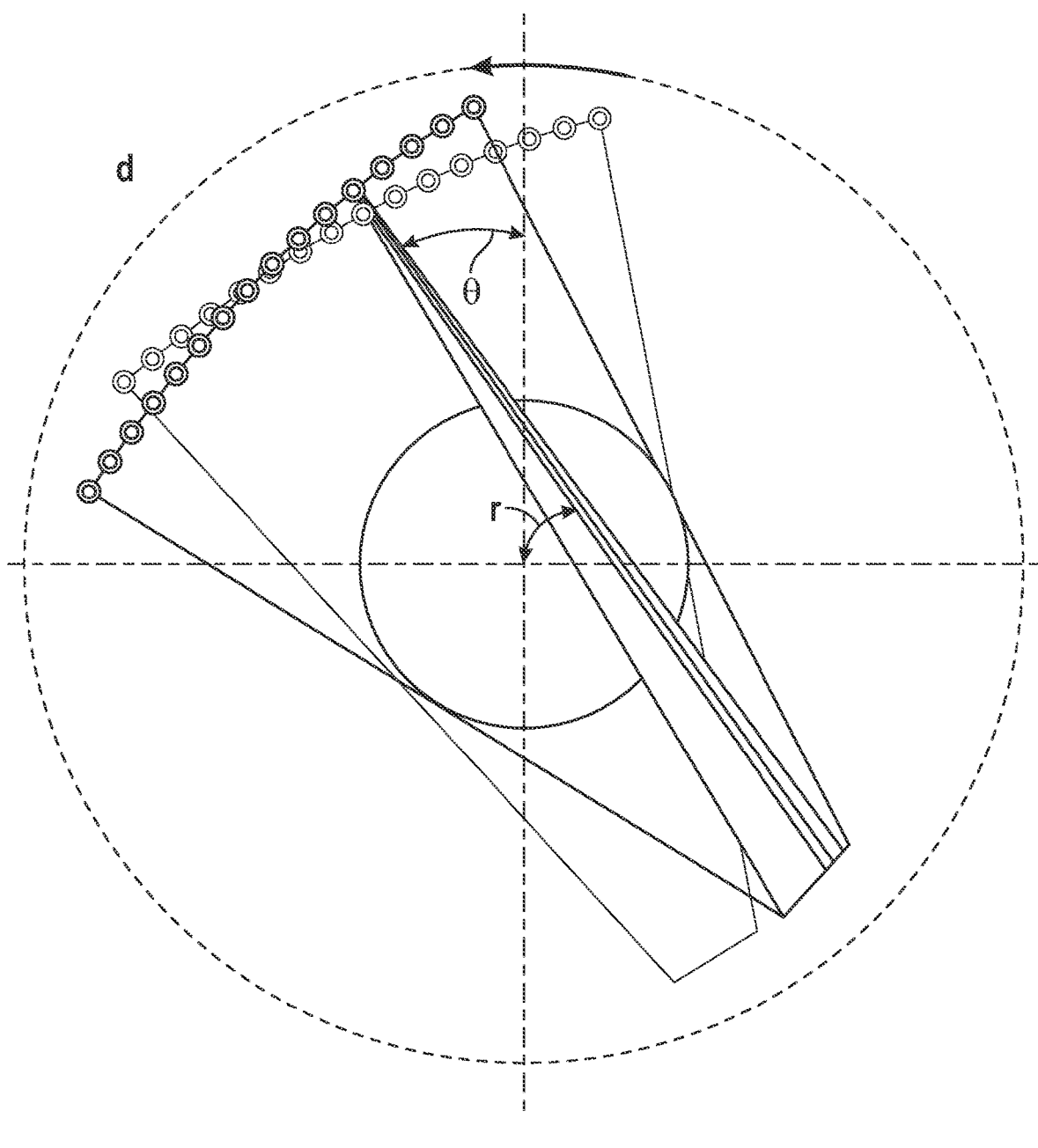
FIG. 7 is a diagram of inverse geometry computer tomography (IGCT) for use with the system of FIG. 1, in accordance with the present disclosure.
Figure 8:
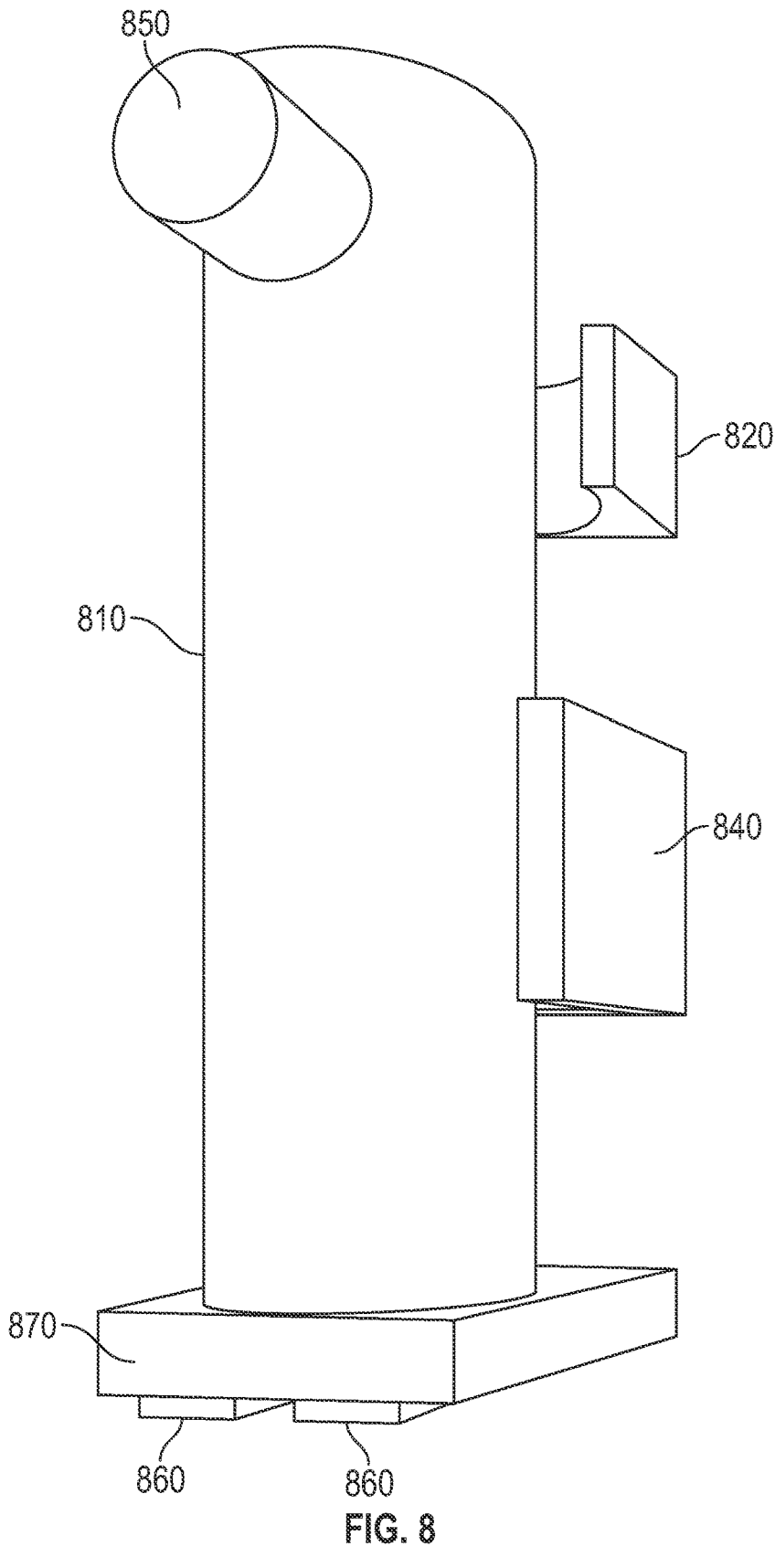
Figure 9:
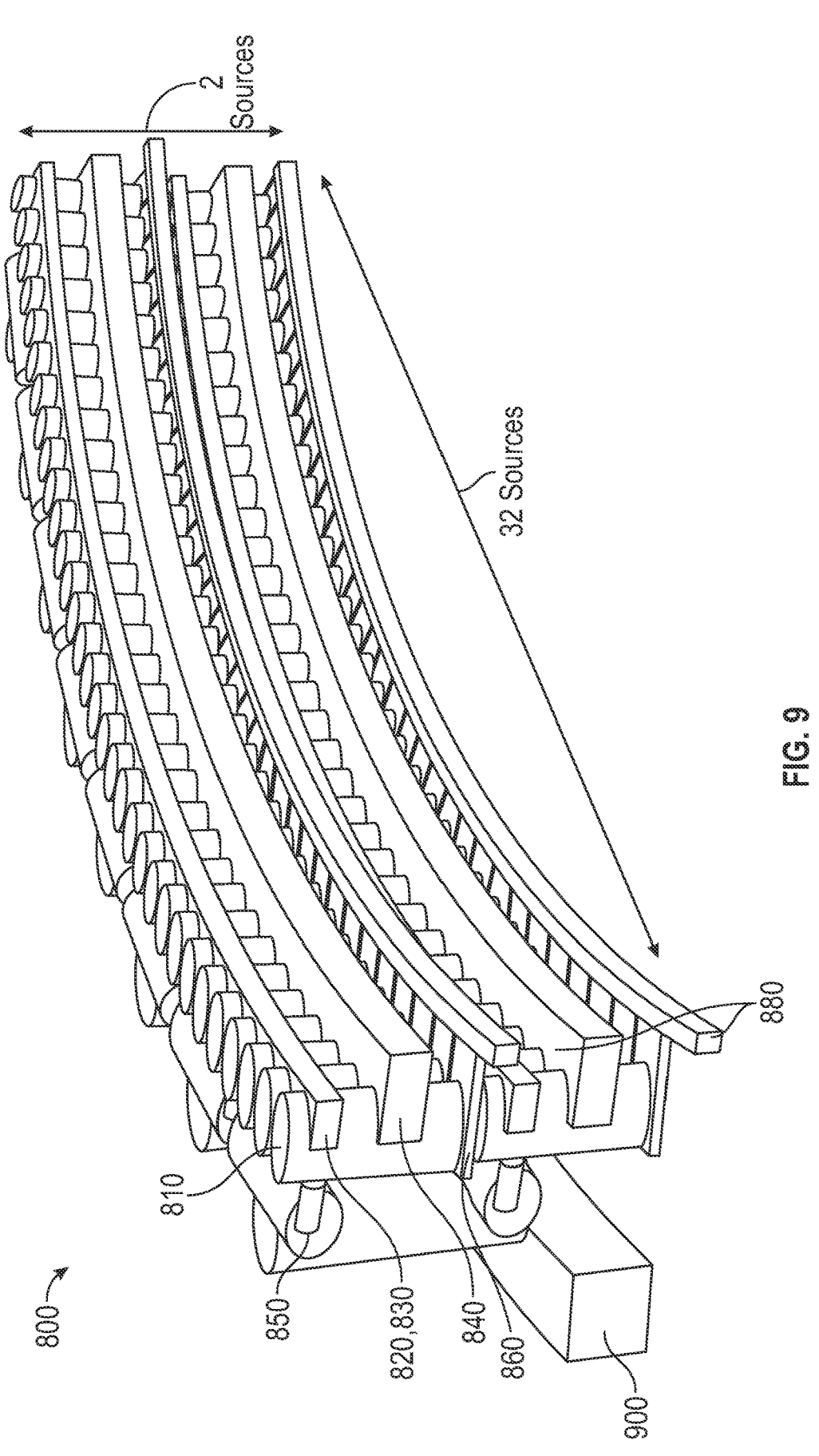
Figure 10:
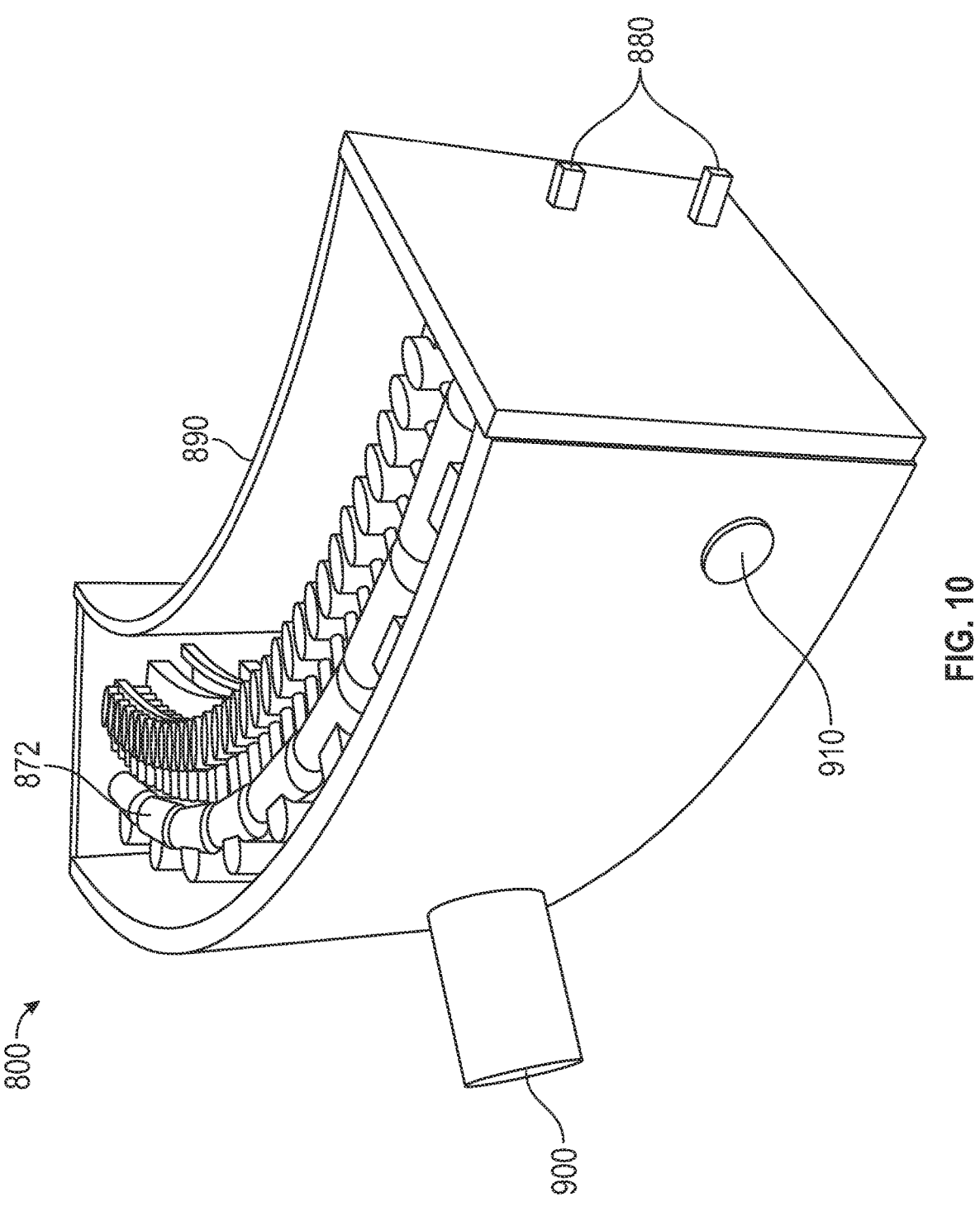
Figure 11:
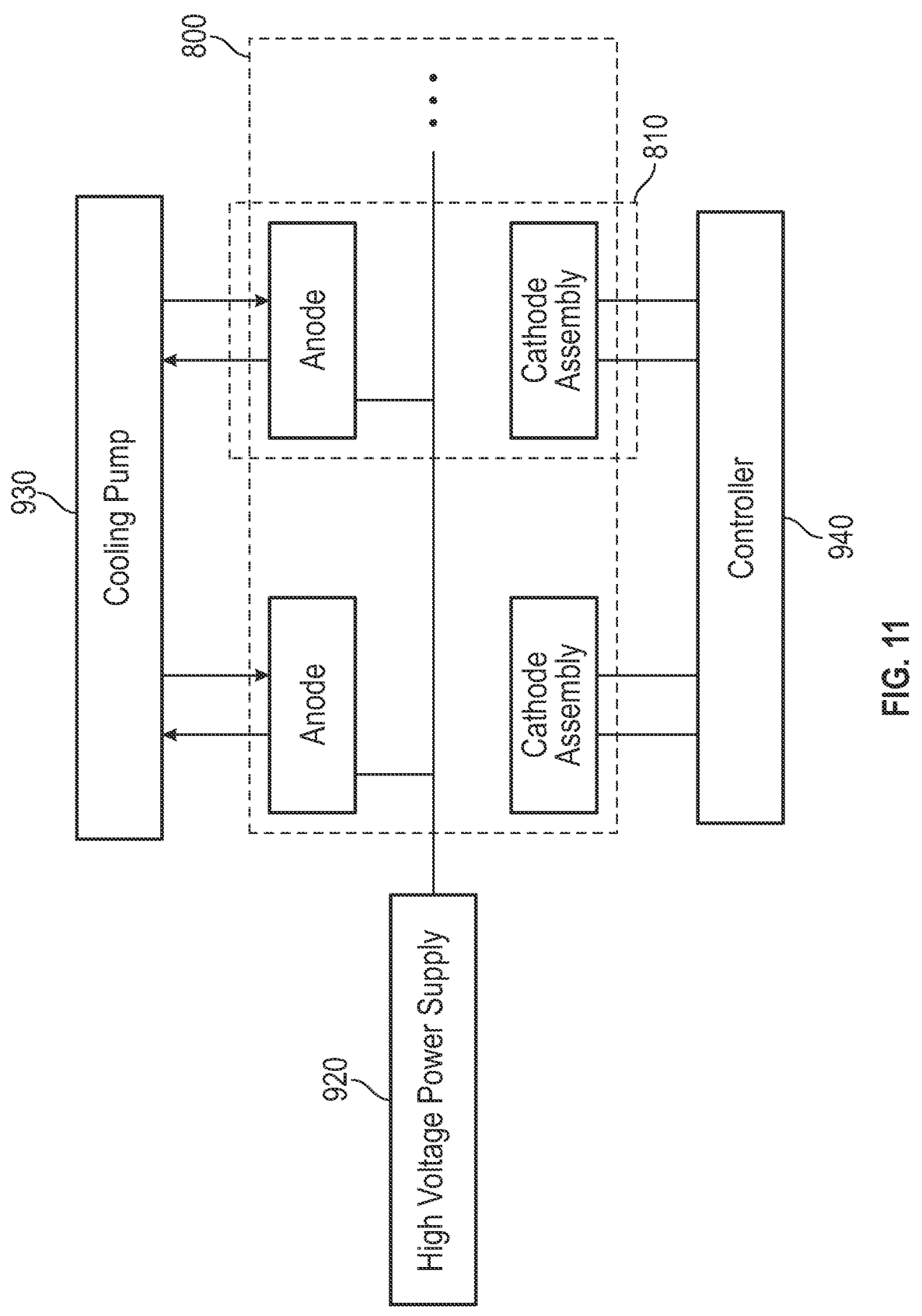

FIG. 8 shows an exemplary an x-ray source for use with the IGCT of FIG. 7, in accordance with the present disclosure;

FIG. 9 shows a side perspective cutaway view of an exemplary 2×32 x-ray source array showing the individual components arrayed, in accordance with the present disclosure;

FIG. 10 shows a side perspective cutaway view of the 2×32 x-ray source of FIG. 9 including some portions of the chassis, in accordance with the present disclosure;

FIG. 11 shows a block diagram of exemplary connections between the x-ray source of FIG. 9 and other sub-systems, in accordance with the present disclosure.

DETAILED DESCRIPTION

The present disclosure relates to a method for building x-ray systems including 2D, tomosynthesis, and computed tomography (CT).

Figure 1:
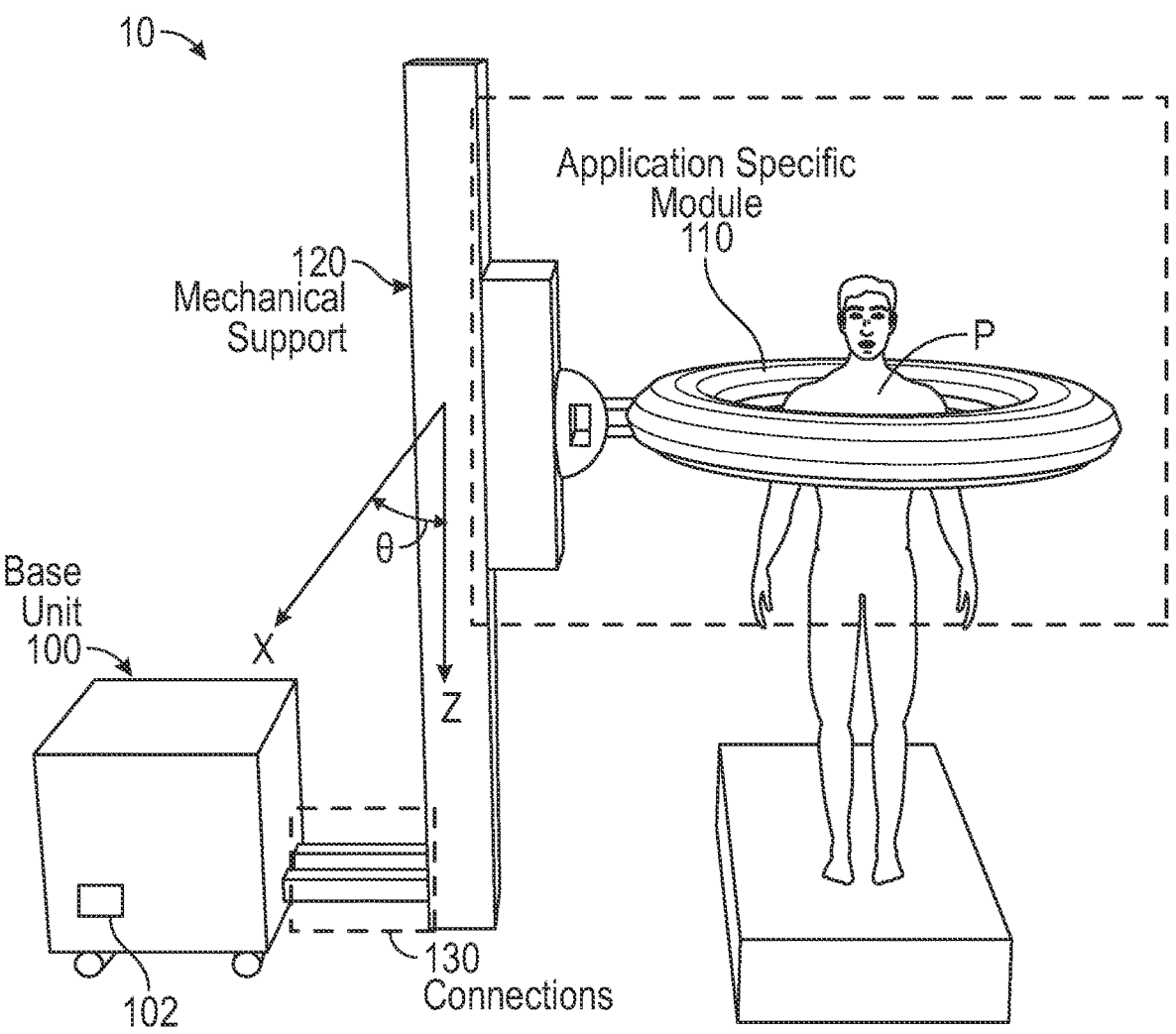
FIG. 1 shows a schematic of the modular x-ray system, in accordance with the disclosure.
Figure 5:
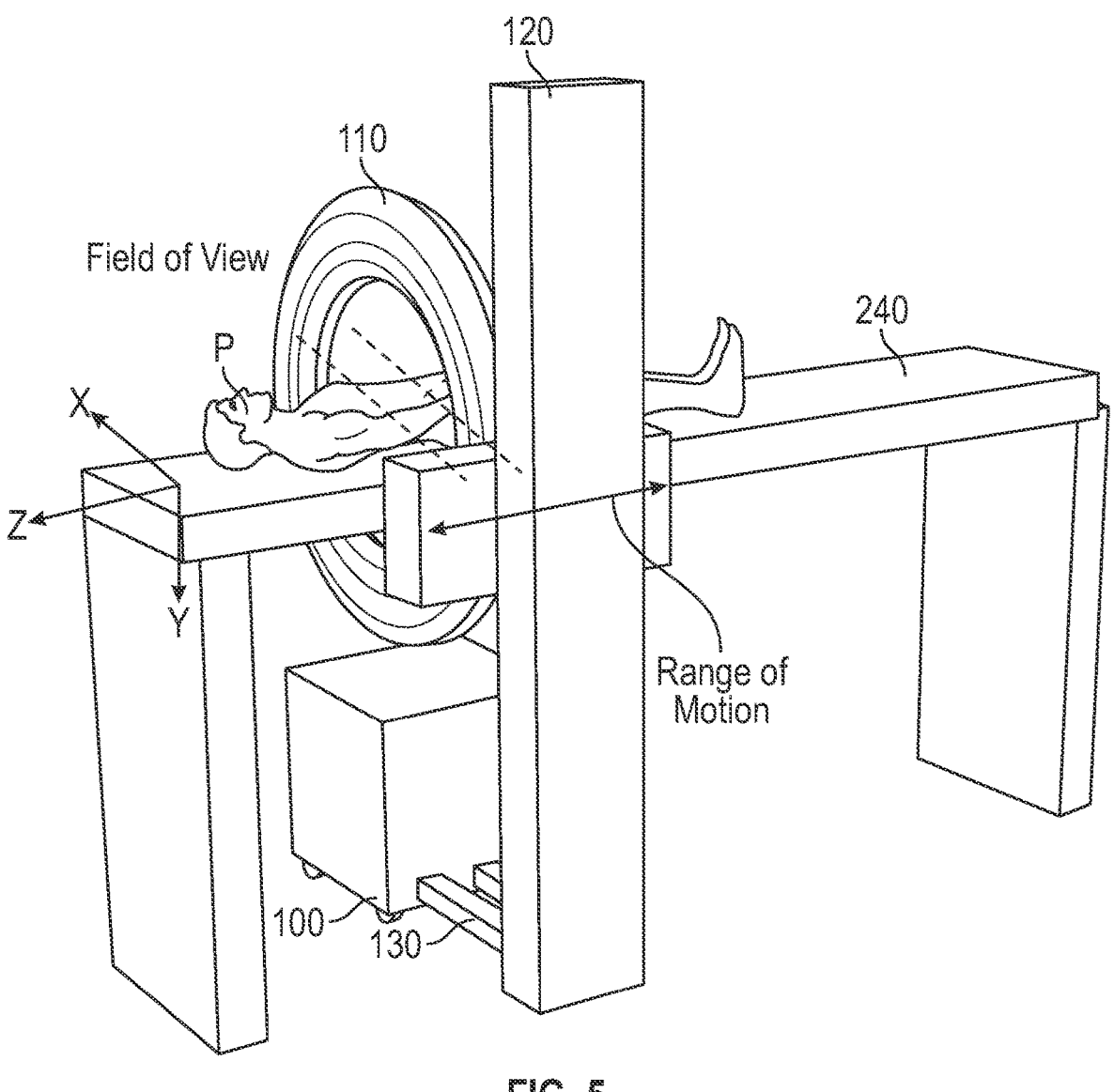
FIG. 5 is a diagram illustrating the system of FIG. 1 in a lateral configuration, in accordance with the disclosure.

FIG. 1 shows a modular x-ray imaging system 10. The modular x-ray imaging system 10 generally includes a base unit 100, an application specific module 110, and a mechanical support 120 for the application specific module 110. The base unit 100 and the application specific module 110 are in communication via connections 130. Some of the connections 130 may be wired or wireless. In aspects, the modular x-ray imaging system 10 can be converted between upright (FIG. 1) and conventional imaging with a patient laying on a bed (FIG. 5).

The mechanical support 120 is used to support the application specific module 110. This mechanical support 120 can be mounted to the ground or be designed to be temporary for easy transportation to improve portability. The mechanical support 120 has the capability of adjusting the height of the application specific module 110 or enabling the application specific module 110 to be rotated, enabling a vertical system to be converted to a lateral system.

In aspects, the base unit 100 may include an x-ray source 102. The base unit 100 may include a miniature x-ray source including of a field emitter using sharpened silicon nanowires, a vacuum package, and a target anode. The x-ray source may include a focusing mechanism and/or a metal plate which protects the field emitter array from ions. The x-ray source is programmable (for example, when used in an array). The x-ray source is high-performance due to the nature of the x-ray source (vacuum transistor). The x-ray source is compact (>10× smaller volume than conventional x-ray sources) and is batch manufacturable utilizing conventional silicon manufacturing technology.

In aspects, the modular x-ray imaging system 10 may include a second application specific module configured for convertible CT which can operate vertically, or laterally, and any angle in-between.

Figure 2:
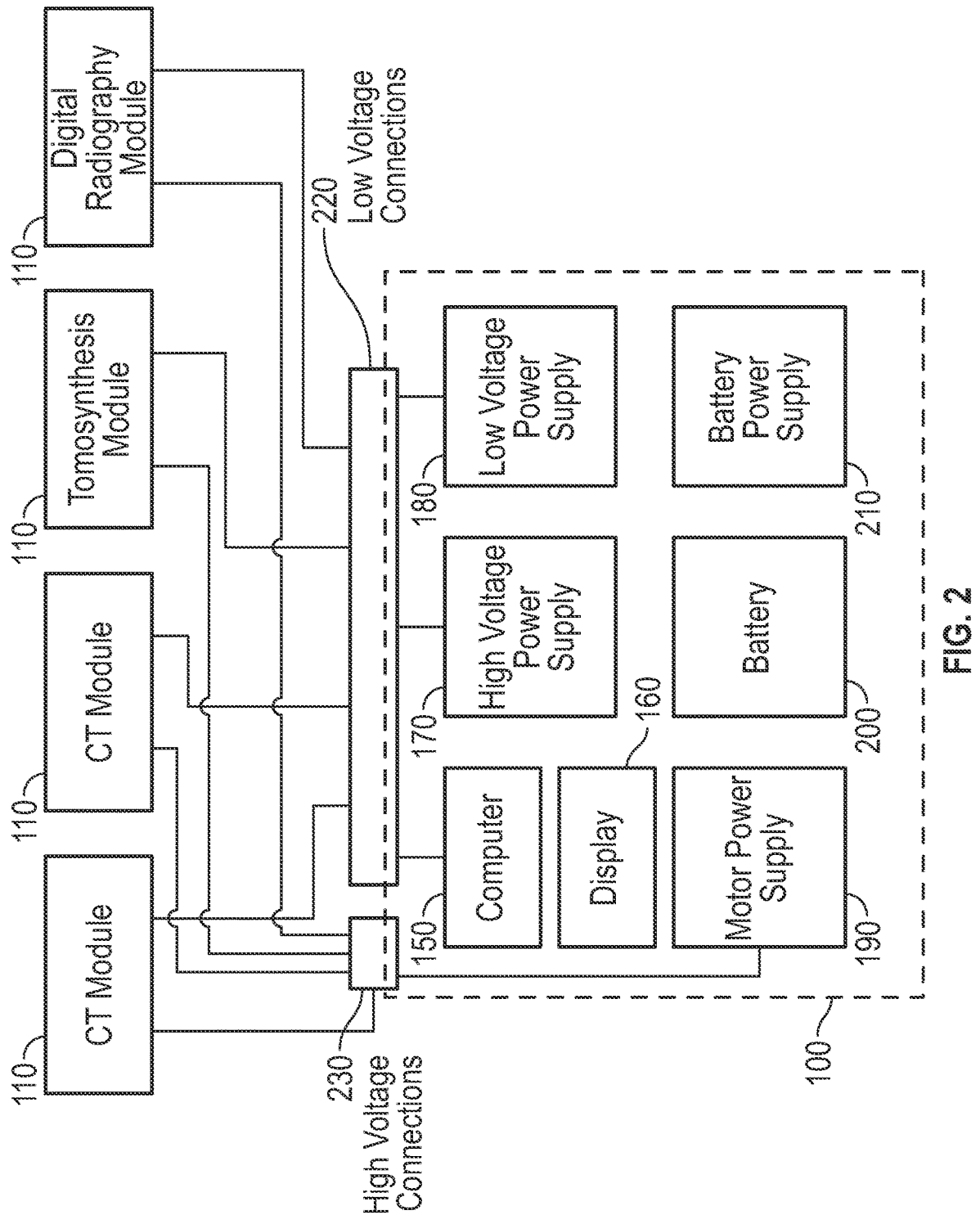
FIG. 2 shows an exemplary block diagram of a base unit of the system of FIG. 1, in accordance with the disclosure.

Referring to FIG. 2, the base unit 100 includes a processor 150, a display 160, a high voltage power supply 170, a low voltage power supply 180, a motor power supply 190, a battery 200, and a battery power supply 210. In various aspects of the disclosure, the processor 150 may include any suitable type of computing device, for example, a laptop, a desktop, mobile device, and/or a server. The processor 150 may include any type of suitable processor such as, without limitation, a digital signal processor, a microprocessor, an ASIC, a graphics processing unit (GPU), a field-programmable gate array (FPGA), or a central processing unit (CPU). The processor 150 may include memory for executing instructions that cause the system to execute various functions.

Figure 3:
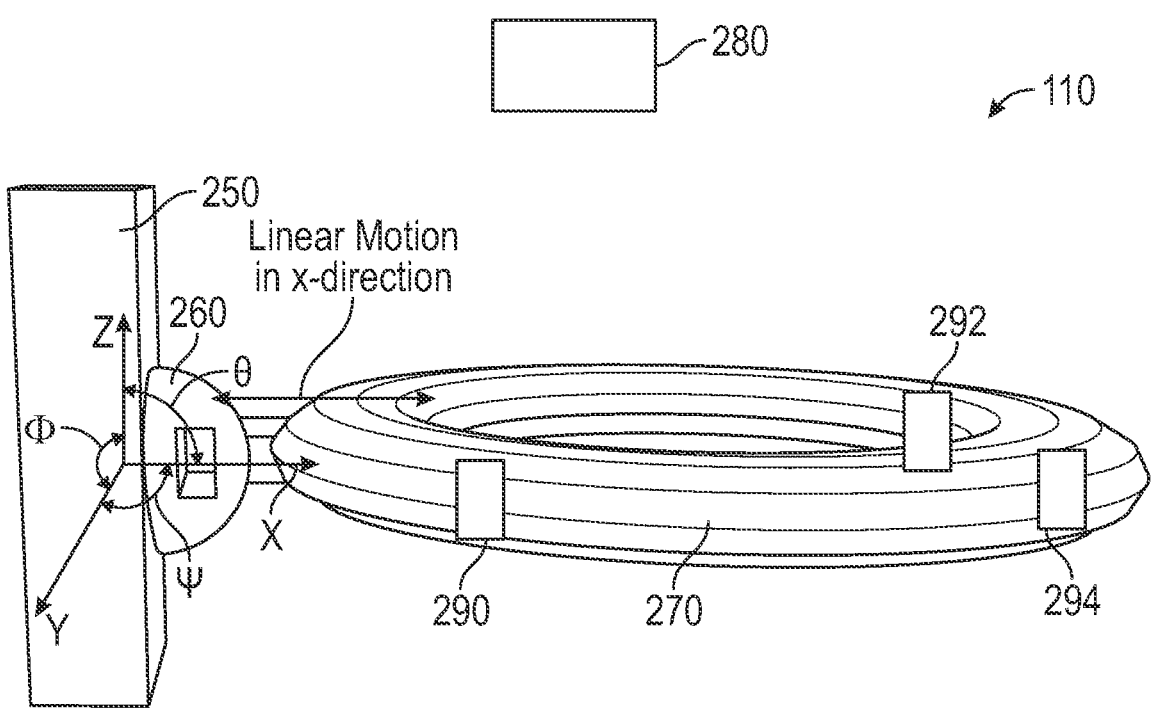
FIG. 3 shows an imaging ring of the system of FIG. 1, in accordance with the disclosure.

The high voltage power supply 170 may supply a voltage greater than 10 kV. The low voltage power supply 180 may supply a voltage less than 10 kV. The low voltage power supply 180 may be configured to turn on and off each individual x-ray source 34 (e.g., x-ray tube) of a plurality of x-ray sources 34 (FIG. 3). The x-ray source(s) 34 is configured to emit a beam including an x-ray spectrum. The motor power supply 190 is configured to power one or more mechanical motors. The base unit 100 may include a plurality of connections 220, 230 to connect different power supplies and communications to one or more application specific modules based upon low or high voltage requirements. The base unit 100 may be designed so that it is portable and rugged with a battery 200 as its temporary power supply and also have a battery power supply 210 to enable charging from an outlet. This would enable the system to operate entirely on its own power if power is interrupted or in the case of field operations. Part of the battery could be replaceable to enable the system power to be replenished if a power outage exceeds its internal battery capacity.

Connections 130 between the application specific module (s) 110 and the base unit 100 may be provided at different voltages which may need to be separated based upon purpose. One or more high voltage connections (>10 kV) 230 connects the high voltage power supply 170 to the application specific module depending on the requirements, and at least one or more low voltage (<10 kV) connections 220 are connected between the motor power supply 190, low voltage power supply 180, and processor 150 to the application specific module 110 to provide control of the x-ray sources 34 and communication between the data acquisition system 292 and the sensors 280 controlling the positioning of the application specific module 110 (FIG. 3). Wireless communication may be used to communicate some information between the processor 150 and different parts of the application specific module 110 to reduce the total number of connections.

Referring to FIG. 3 the application specific module 110 is shown. The application specific module can be any subsystem module designed for any x-ray imaging modality such as 2D digital radiography, tomosynthesis (e.g., chest and breast tomosynthesis), or computed tomography. The application specific module 110 includes components specific to the application (e.g., CT module, tomosynthesis module, and/or digital radiography module). The application specific module 110 generally includes an imaging ring 270, sensors 280, and motorized controls 260. In aspects, the application specific module 110 may include a motorized track 250 to move the motorized controls 260 and the imaging ring 270. The motorized controls 260 may be further configured to control the movement of the imaging ring 270 in the x-y plane of the patient using at least one linear degree of motion and/or at least one angular degree of freedom. The application specific module 110 may be configured to be adjusted in height and/or rotation relative to the normal of a mounting surface of the application specific module 110.

The motorized track 250 may be configured to move the application specific module 110 a distance larger than the desired imaging field of view and less than the length of the full body of the patient P. The motorized track 250 may be further configured to be rotated around an axis normal to a surface of contact with the mechanical support 120 in order to change a direction of motion.

Figure 4:
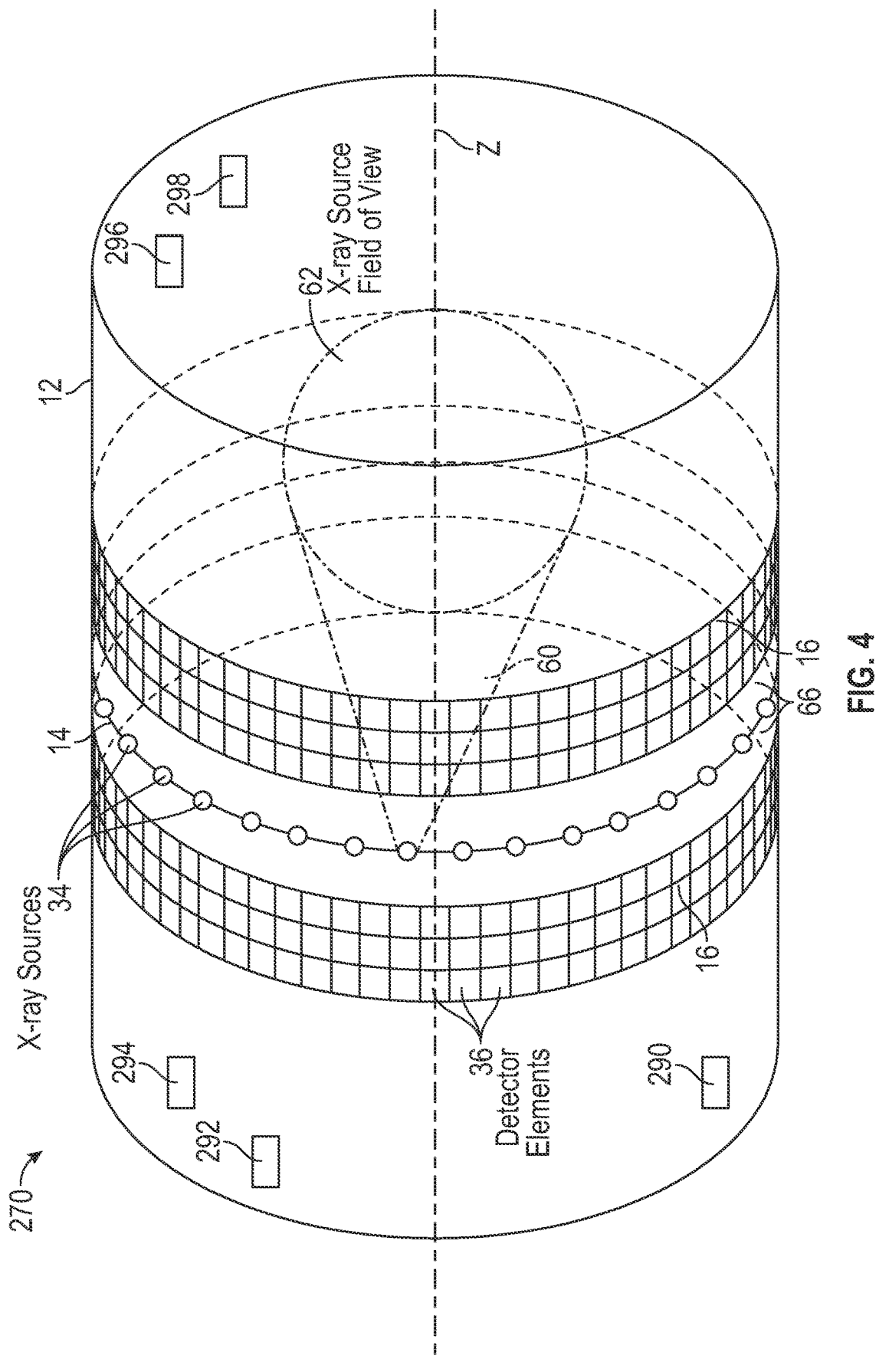
FIG. 4 shows a diagram of the imaging ring of FIG. 3, in accordance with the disclosure.

The imaging ring 270 is configured to capture images. The imaging ring 270 includes a controller 290, a plurality of x-ray sources 34, one or more anti-scatter grids 16, a data acquisition system 292, x-ray detectors 36 (e.g., photon counting or energy integrating), communication system 294, and sensors 280 for positioning the imaging ring 270 (FIG. 4). The anti-scatter grid 16 is configured for limiting the amount of scattered radiation reaching the detector, thereby improving the quantity of x-ray images. The one or more anti-scatter grids 16 may include a dynamic anti-scatter grid or a moving anti-scatter grid with a plurality of x-ray sources to optimally remove scatter from each x-ray source 34.

The imaging ring 270 may further include components associated with the x-ray sources 34 such as x-ray collimators 296 and/or x-ray filters 298. The communication system 294 is configured for communication between the application specific module 110 and the base unit 100 (FIG. 1). The x-ray collimator 296 is generally placed close to the x-ray source 34 to restrict the span of the x-ray beam. The x-ray filter 298 is configured to selectively attenuate, or block, low-energy rays during x-ray imaging.

The motorized controls 260 are configured to provide motion for imaging and to automatically capture the correct images. The motorized controls 260 may provide mechanical alignment of the ring to the patient P. The sensors 280 are configured for sensing position data and for enabling positioning the patient P relative to the imaging ring 270.

The controller 290 is configured for controlling the output x-ray sources 34 (FIG. 4). The controller 290 may include any type of suitable processor such as, without limitation, a digital signal processor, a microprocessor, an ASIC, a graphics processing unit (GPU), a field-programmable gate array (FPGA), or a central processing unit (CPU). The controller 290 may include memory for executing instructions that cause the system to execute various functions.

The imaging ring 270 is moved along the z-axis or the height of the patient P to capture an image with a sufficient field of view through a motorized track 250. The motorized track 250 has a range of motion larger than the desired image field of view but less than the entire length of the body of the patient P. The motorized track 250 is used when the field of view requirements are larger than the field of view provided by the x-ray detectors 36. The motorized controls 260 can enable a combination of motions to position the imaging ring 270 in the optimal orientation relative to the patient P. Motorized controls 260 can handle the motion in the x-y plane through a combination of movements in the x-direction, and one or more angular directions of $\theta$, $\psi$, and $\Phi$; the axes of motion are shown in FIG. 3. The imaging ring 270 includes a sufficient number of x-ray sources 34 to meet the power requirements of the desired scan and has a sufficient angular coverage by both the x-ray sources and x-ray detectors 36 to be considered computed tomography. One or more anti-scatter grids 16 (FIG. 4) are configured to reduce the x-ray scatter. The anti-scatter grid 16 may be dynamic or movable to adjust based upon which x-ray source is currently operational. Finally, sensors 280 such as cameras may be used to optimally position the imaging ring relative to the patient P.

This design change is enabled by using "stationary" imaging for 3D imaging where a plurality of x-ray sources 34 illuminate a detector array composed of x-ray detector elements 36 larger than the field of view of an individual x-ray source 62; an example of a stationary CT layout is shown in FIG. 4. This system replaces a single x-ray tube and a detector array is being moved relative to the patient requiring strong mechanical supports to move the components, generally heavier than 1000 kg. The removal of the motion, the multiple components, and the difference in the size and weight of the x-ray source enable the x-ray imaging system to be broken up into smaller components. This design change enables multiple x-ray systems to utilize a common base unit reducing the cost, size, weight, and footprint of the overall combined systems, and enables more portability by only requiring part of the system be transferred at one time. The base unit can be transferred to a location with an already mounted application specific module or, alternatively, a new application specific module can be brought in if additional capability is required.

A computed tomography system can be realized using this system design which has the benefits through the modularity or separation of the individual components and a decrease in the overall weight of the application specific module. The modularity and separation of the individual components enables the system to be transported in separate pieces which can be more easily moved and in a smaller vehicle. The reduction in weight enables a convertible CT which can operate as a vertical oriented CT (FIG. 5) or a horizontal oriented CT (FIG. 1), scanning at a conventional lateral angle or at angle θ in-between vertical and lateral.

Operation as a vertical CT enables the operator to save on footprint as the room no longer requires the need to support the length of a patient, thus saving on the areal cost for the room and the bed of the CT. While the CT is operating in the conventional lateral configuration, an x-ray transparent table 240 supports the patient with the table supported by at least two points, each on a different half of the table with an opening for the region of interest of imaging. The table with two points of support is enabled by the fact that the bed does not need to provide the motion of the patient relative to the ring, and can now be portable in form-factor (e.g., folding), supporting more weight and being less costly.

Figure 6:
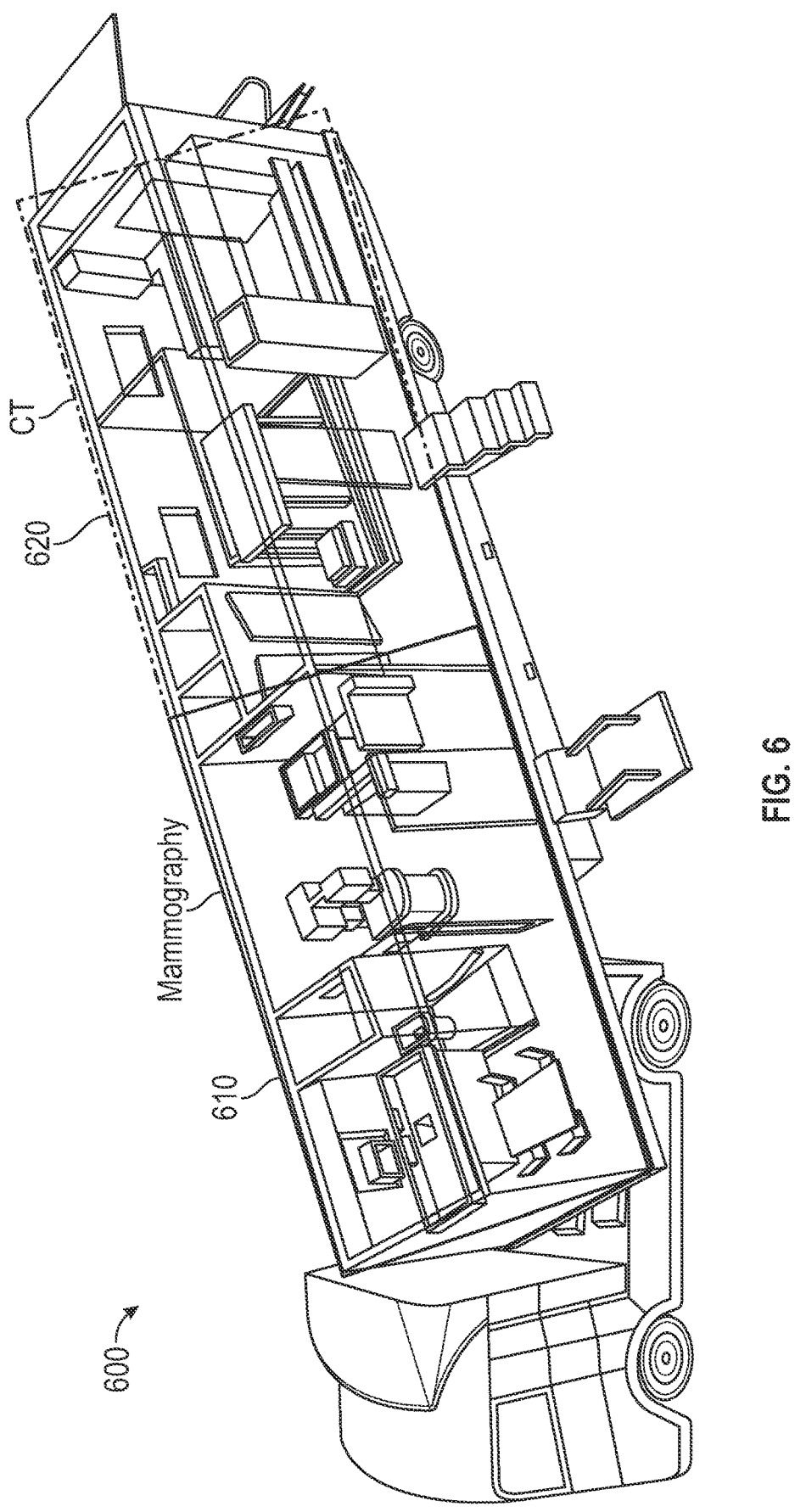
FIG. 6 is a diagram illustrating a mobile screening system, in accordance with the disclosure.

Referring to FIG. 6 a diagram that illustrates an example of a mobile screening system 600 is shown. The mobile screening system 600 may include a truck and a mammography 610 and/or a computed tomography system 620. The mobile screening system 600 includes more than one imaging modality. The mobile screening solution constitutes a vehicle (e.g., a truck or bus) which includes x-ray imaging equipment, additional equipment, and shielding. The mobile screening system has the benefit of reducing the overall cost of ownership of the system, a key challenge for running mobile medical imaging. Another advantage of the mobile screening system having more than one imaging modality like the one described is: 1) the mobile screening system improves the profitability of the operator by up to 40% by saving on personnel, hardware, and/or maintenance costs; 2) the mobile screening system improves patient convenience by allowing patients to be screened for more than one illness; and 3) the mobile screening system reduces the overall required infrastructure to maintain (one bus vs. the total number of individual buses). The modular x-ray imaging system 10 may be used as an upright and modular CT system, in accordance with the disclosure. The upright and modular CT system may be used for mobile screening (FIG. 6) and/or fixed screening.

A stationary CT system breaks the conventional trade-off between the rotation speed of the x-ray tube and detector pair around the gantry compared to the imaging speed of the patient. This requires that the gantry spins at an increasing rate for a reduced detector size or increased scan rate. Due to the electronic rastering of a stationary CT, the "gantry" rotation is now orders of magnitude faster compared to conventional CT enabling high scan speeds with a small detector to save on cost or higher throughput imaging for the same system specifications.

FIG. 7 is a diagram of inverse geometry computer tomography for use with the system of FIG. 1. The disclosed technology provides a geometrical layout to fix the fundamental trade-off between detector size and field-of-view is the usage of inverse geometry imaging where multiple x-ray sources illuminate different areas of the desired image onto a smaller detector, and the images are stitched together to form the desired field-of-view. This fundamentally changes the cost-equation to building any x-ray imaging system. For CT systems: the cost of the x-ray source module and detector area should be optimized for a given field-of-view. Inverse geometry x-ray imaging may be used for 2D x-ray imaging or tomosynthesis and computed tomography showing clear benefits such as reduced dose, improved image quality by reducing cone-beam artifacts, and reductions in the necessary detector size for a given field of view thereby reducing detector cost. The reduction in cost and detector area can also be used to offset other increases in costs such as more expensive detectors which are photon energy sensitive or with improved spatial resolution, and for other system geometries such as stationary CT or CT performed without moving parts. The disclosed technology provides the benefit over previous demonstrations of inverse geometry systems that used a single vacuum chamber with multiple x-ray sources integrated together causing the challenges listed above. In FIG. 7, an array of x-ray sources illuminates a small detector capturing part of the field of view. The complete field-of-view is formed when all of the x-ray sources have illuminated the detector, and the image is stitched together. The array of x-ray sources and the detector rotate in-sync with each other and an image is taken at every angle, theta.

The disclosed technology provides a solution to implementing inverse geometry effectively by producing high-performing, compact, and inexpensive x-ray sources. High x-ray fluxes and fast on/off times (<about 100 μs) are required for high-performance CT and the main challenge of inverse geometry CT. Tight x-ray source pitch is necessary to minimize the size of the detector as the x-ray images must overlap to get the desired x-ray fluxes in certain regions of the image. Finally, the cost for each source must be inexpensive as to make the cost-optimization between the x-ray source and detector size to be favorable. These properties are addressed in the disclosed technology.

Referring to FIGS. 8-10 a sub-system x-ray source module 800 is shown. The sub-system x-ray source module 800 generally includes multiple individually packaged x-ray sources 810 with one or more focal spots, one or more filters 820, a collimator 830 and/or an x-ray source alignment apparatus 840. Each x-ray source 810 includes two types of connections: an electrical connection between the emitter and gate of the field emission electron source 860 with the controller, and an electrical connection between the high voltage power supply 850 (e.g., a voltage above about 10 k volts) and the anode designed to accelerate the electrons to generate x-ray through Bremsstrahlung. Bremsstrahlung is electromagnetic radiation produced by the deceleration of a charged particle when deflected by another charged particle, typically an electron by an atomic nucleus. X-ray sources may have a physical or electronic indicators 870 to show operators whether or not the x-ray sources need to be replaced. The connection to the anode may also carry the cooling liquid to actively remove the heat generated from electrons colliding with the anode. The individualized x-ray source 810 (e.g., x-ray tube) and its components are repeated to form an array of x-ray source required for an inverse geometry CT. These individual components are then interconnected through high voltage and cooling interconnects 900 and a common low voltage connections 880 (FIG. 9). These connections are output of the leak-proof outer case or chassis 890 (FIG. 10) through a common high voltage and cooling out, and through the common low voltage connections.

With further reference to FIGS. 9 and 10 the entire sub-system x-ray source module 800 may be electrically isolated by immersing connections and the x-ray sources in insulating, dielectric fluid. This fluid and all of the sub-components are contained through a leak-proof outer case that has one or more connections to drain and fill the sub-system module with dielectric fluid, provide electrical connections between the x-ray sources, controller and high voltage power supply, and provide insulating dielectric fluid to cool the anode.

FIG. 11 shows a block diagram of the connections between the sub-system x-ray module 800 and other sub-systems such as the high voltage source 920 (voltage >about 10 kilovolts), cooling pump 830, and a controller 840.

Multiple x-ray source sub-systems 800 may be located on the same system and connected to one or more high voltage power supplies 820, cooling pump 830 and controller 840. By utilizing multiple x-ray source sub-systems 800, the speed of motion for the system 800 can either be eliminated in the case of stationary imaging or reduced for conventional CT which reduces the mechanical engineering requirements for such a system 800. The controller 840 is configured to control each x-ray source 810 independently. Each x-ray source 800 has an independent calibration profile which is applied at both the x-ray source and detector image. The calibration ensures that each x-ray source 810 is outputting the proper dose and detector-side calibration mitigates any fine misalignment between the x-ray source 810 and detector. The proper dose may be determined using scout x-ray images or using other sensors which provide information necessary to estimate the overall dose. The cumulative x-ray flux emitted by the x-ray source 810 is dynamic as a function of both position and time. The x-ray flux profile can be adjusted by changing the power of each x-ray source 810 or the amount of time that each x-ray source 810 is on.

Certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The aspects disclosed herein are examples of the disclosure and may be embodied in various forms. For instance, although certain aspects herein are described as separate aspects, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed. Like reference numerals may refer to similar or identical elements throughout the description of the figures.

The phrases "in an aspect," "in aspects," "in various aspects," "in some aspects," or "in other aspects" may each refer to one or more of the same or different example Aspects provided in the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A modular x-ray imaging system, comprising:
an application specific module including:
an imaging ring configured to image a patient, the imaging ring including:
a plurality of x-ray sources configured to generate and emit a beam including an x-ray spectrum;
one or more collimators configured to restrict a span of an x-ray beam;
one or more filters configured to selectively attenuate, and/or block low-energy rays during x-ray imaging; and
one or more x-ray detectors configured to detect x-rays generated by the plurality of x-ray sources;
a sensor configured to provide positioning data to enable positioning of the imaging ring relative to the patient;
a motor configured to position the imaging ring based on the sensed position; and
a controller for controlling an output of the plurality of x-ray sources;
a base unit in communication with the application specific module, the base unit including:
a first power supply having an output voltage greater than 10 kV;
a second power supply having an output voltage less than 10 kV, configured to turn on and off each individual x-ray source of the plurality of x-ray sources;
a processor; and
a memory including instructions stored thereon which, when executed by the processor, cause the modular x-ray imaging system to:
position the imaging ring based on the sensor; and
capture imaging data; and
a mechanical support configured to support the imaging ring.

2. The modular x-ray imaging system of claim 1, wherein the base unit further includes a battery, and wherein the base unit is configured to operate solely on battery power with part of the battery being able to be changed during operation to maintain battery power longer than a total capacity of the battery.

3. The modular x-ray imaging system of claim 1, wherein the base unit is configured to move independently of the rest of the modular x-ray imaging system.

4. The modular x-ray imaging system of claim 1, wherein the base unit is configured to be connected to, control, and power multiple application specific modules simultaneously.

5. The modular x-ray imaging system of claim 1, further comprising a second application specific module configured to provide convertible computed tomography (CT) which can operate vertically, or laterally, and any angle in-between.

6. The modular x-ray imaging system of claim 1, wherein the application specific module is operated as at least one of a vertical or a horizontal CT.

7. The modular x-ray imaging system of claim 5, wherein when operating laterally, the modular x-ray imaging system further includes an x-ray transparent table configured to support a patient with the x-ray transparent table supported by at least two points each on a different half of the table with an opening for a region of interest for imaging.

8. The modular x-ray imaging system of claim 5, wherein the second application specific module further includes:
  motorized controls;
  an imaging ring including a controller, a plurality of x-ray sources, one or more anti-scatter grids, x-ray detectors, and communication electronics;
  a motorized track configured to move motorized controls and the imaging ring; and
  a sensor configured to determine positioning of the imaging ring relative to the patient,
  wherein the motorized controls provide a mechanical alignment of the imaging ring to the patient.

9. The modular x-ray imaging system of claim 8, wherein the motorized track is configured to move the second application specific module a distance larger than a desired imaging field of view and less than a length of a full body of the patient.

10. The modular x-ray imaging system of claim 8, wherein the motorized track is configured to be rotated around an axis normal to a surface of contact with the mechanical support in order to change a direction of motion.

11. The modular x-ray imaging system of claim 8, wherein the motorized controls are further configured to control a movement of the imaging ring in an x-y plane of the patient using:
  at least one linear degree of motion; or
  at least one angular degree of freedom.

12. The modular x-ray imaging system of claim 1, further comprising at least one of a dynamic anti-scatter grid or a moving anti-scatter grid with a plurality of x-ray sources to optimally remove scatter for each x-ray source.

13. The modular x-ray imaging system of claim 1, wherein the application specific module is configured to be adjusted in height and/or rotation relative to the normal of a mounting surface of the application specific module.

14. The modular x-ray imaging system of claim 8, further comprising:
  a data acquisition system; and
  at least one of a wired or a wireless connection between the application specific module and the base unit, the at least one of a wired or a wireless connection including:
  at least one high voltage connection of greater than 10 kV configured to connect the first power supply to the application specific module; and
  at least one more low voltage connections of less than 10 kV configured to connect between the power supply configured for powering the motors, the second power supply, and the processor to the application specific module to provide control of the x-ray sources and communication between the data acquisition system and the sensors controlling the positioning of the application specific module.

15. A modular x-ray imaging system, comprising:
an application specific module including:
  a vertically positionable imaging ring configured to image a patient;
  a processor; and
  a memory including instructions stored thereon which, when executed by the processor, cause the modular x-ray imaging system to:
    position the imaging ring; and
    capture imaging data; and
a base unit in communication with the application specific module, and configured to power the application specific module, the base unit including:
  a first power supply having an output voltage greater than 10 kV;
  a second power supply having an output voltage less than 10 kV, configured to turn on and off each individual x-ray source of the plurality of x-ray sources; and
a mechanical support configured to support the vertically positionable imaging ring wherein the base unit and application specific module are configured to communicate in at least one of a wired and/or wireless manner.

* * * * *